US006440166B1

(12) United States Patent
Kolluri

(10) Patent No.: US 6,440,166 B1
(45) Date of Patent: Aug. 27, 2002

(54) MULTILAYER AND MULTIFUNCTION VASCULAR GRAFT

(76) Inventor: Omprakash S. Kolluri, 2305 Cervantes Way, Campbell, CA (US) 95008

(*) Notice: Subject to any disclaimer, the term of this patent is extended or adjusted under 35 U.S.C. 154(b) by 0 days.

(21) Appl. No.: 09/505,415

(22) Filed: Feb. 16, 2000

Related U.S. Application Data

(60) Provisional application No. 60/120,263, filed on Feb. 16, 1999.

(51) Int. Cl.[7] .................................................. A61F 2/06
(52) U.S. Cl. ........................ 623/1.4; 623/1.42; 623/1.43
(58) Field of Search ................................ 623/1.42–1.46

(56) References Cited

U.S. PATENT DOCUMENTS

| | | | |
|---|---|---|---|
| 4,842,576 A | | 6/1989 | Hoffman, Jr. et al. ......... 600/36 |
| 5,413,597 A | * | 5/1995 | Krajicek .................... 623/1.44 |
| 5,584,876 A | | 12/1996 | Bruchman et al. ............. 623/1 |
| 5,643,712 A | | 7/1997 | Brasile ...................... 435/1.2 |
| 5,723,291 A | | 3/1998 | Kushner et al. ............... 435/6 |
| 5,735,897 A | | 4/1998 | Buirge ......................... 623/12 |
| 5,851,229 A | | 12/1998 | Lentz et al. .................... 623/1 |
| 5,858,556 A | | 1/1999 | Eckert et al. ............... 428/586 |
| 5,879,383 A | | 3/1999 | Bruchman et al. ............. 623/1 |
| 5,880,090 A | | 3/1999 | Hammond et al. .............. 514/2 |
| 5,908,449 A | * | 6/1999 | Bruchman et al. ......... 623/1.44 |
| 5,968,092 A | * | 10/1999 | Buscemi et al. ........... 623/1.44 |
| 6,096,070 A | * | 8/2000 | Ragheb et al. ............. 623/1.46 |
| 6,179,817 B1 | * | 1/2001 | Zhong ........................ 604/265 |

OTHER PUBLICATIONS

Wagner, Tiffany, Thompson, Shultz, and Johnson, in *Transactions, Society of Biomaterials*, 1994.
Guidoin et al,*ASAIO Journal* Nov–Dec; 42, 1996.
Clapper et al, S*ymposium, Society for Biomaterials*, 1994.
Werkmeister et al, *Transactions, Society for Biomaterials*, Apr. 1994.
Termin et al, *Transactions, Society for Biomaterials*, Apr. 1994.
Greisler et al, Biomaterials 1996, vol. 17, No. 3.
Greisler et al, *Surfaces in Biomaterials Symposium*1994.

* cited by examiner

*Primary Examiner*—Dasvid H. Willse
*Assistant Examiner*—Suzette Jackson
(74) *Attorney, Agent, or Firm*—Carol D. Titus; James J. Leary

(57) ABSTRACT

A multi-zone, multifinctional graft with two or more zones that have different chemical and biological characteristics is provided. The vascular conduit that has of an inner zone that is permanently non-thrombogenic and anti-proliferative, and one or more outer zones that allow for beneficial tissue in-growth and sealing of the graft to prevent leakage. The small diameter vascular conduits of the present invention containing these different zones may be fabricated from woven or knitted Dacron, extruded porous PTFE, from polyurethane polymer, or other similar materials, and the structure of these conduits so modified as to provide these different zones. One embodiment contains an inner non-thrombogenic layer and an outer thrombogenic layer, optionally containing a growth agent. A second embodiment contains a third intermediate layer having a growth agent impregnated therein.

36 Claims, 1 Drawing Sheet

MULTILAYER AND MULTIFUNCTION VASCULAR GRAFT

CROSS REFERENCE TO OTHER APPLICATIONS

This application claims the benefit of U.S. Provisional Patent Application No. 60/120,263, filed Feb. 16, 1999.

FIELD OF THE INVENTION

The present invention relates to synthetic vascular grafts, and in particular, to multi-zone and multifunctional synthetic vascular grafts, thereby improving the biocompatibility and long term patency of synthetic vascular grafts.

BACKGROUND OF THE INVENTION

Synthetic vascular grafts form an important therapeutic component to replace diseased arteries and thus save an important organ, limb, or in many cases, the life of the patient. Most synthetic vascular grafts are tubular structures that geometrically mimic the native blood vessel that it is meant to replace. While a natural blood vessel consists of many layers intimately joined together, synthetic vascular conduits are of a monolithic construction consisting of only one layer. These tubular structures are generally fabricated out of knitted or woven Dacron polyester yarns or they are extruded polyurethane tubes or extruded PTFE tubes with defined porosities in the wall of the extruded tube. It is important to recognize that in the case of structures that are woven or knitted from Dacron polyester yarn or fabricated from extruded PTFE tubes with porous walls, the porous nature of these structures is both a benefit and a detraction. The porous walls of these devices are designed to promote tissue in-growth under the proper environment, thus integrating the graft into the surrounding tissue. Studies by other investigators have resulted in currently marketed products that have a wall pore size of approximately 20 μm. The porous walls also result in blood leakage unless they are sealed. Several approaches are used to seal these grafts. One approach is to pre-clot the graft with the patient's blood. A second method uses impregnation of the graft with pure bovine collagen. The bovine collagen, which is similar to human collagen, a member of the basement membrane family of human tissue, promotes clotting and thus prevents leaks. A third method uses a topical application of the blood coagulant, thrombin, mixed with cryoprecipitate. While the primary purpose of these coatings is to seal the exterior of porous grafts, a further objective in all these methods is to improve the biocompatibility of the grafts.

All the approaches described above suffer some basic disadvantages that prevent the use of these types of coatings in fabricating small diameter synthetic grafts for replacing diseased vessels, particularly in peripheral applications below the knee and in coronary applications. While these problems also exist in larger diameter synthetic grafts such as those with internal diameter 6 mm and above, the problem is particularly acute in small diameter conduits. For the purpose of this invention, small diameter synthetic vascular conduits are defined as those with internal diameter ≦5 mm.

The specific problem associated with all the approaches described so far is their inability to maintain long-term patency of the graft. Over time the internal diameter of these grafts continues to decrease, eventually shutting off the blood flow. This phenomenon can occur in periods as short as three weeks or may occur over a period of several years. The problem occurs because the grafts prepared by the three methods described above create a reactive surface on the inner lumen of the graft, leading to several biological events including thrombosis, platelet aggregation leading to the formation of white thrombus, and proliferation of smooth muscle cells leading to intimal thickening and a reduction in the lumen diameter. The latter problem of smooth muscle cell proliferation is particularly problematic at the anastomosis site where the grafts are sutured to the native vessel.

Studies by Wagner, Tiffany, Thompson, Shultz, and Johnson of the Department of Surgery at the University of Pittsburgh, reported in *Transactions, Society of Biomaterials*, 1994, have shown that thrombin, topically applied to the external surface of the graft retains its activity in excess of 300 days and that this activity is resistant to both heparin and hirudin, which are potent anti-coagulants. Any migration of these thrombotic agents can have disastrous consequences by promoting thrombosis and plugging the vascular conduit being repaired.

Several approaches have been tried in an effort to maintain anti-coagulant behavior of the interior surface of the graft and ensure long-term patency. The inner surface of native blood vessels are lined with a layer of endothelial cells that maintain the surface in a non-thrombogenic state except when there is injury to the vasculature. In order to mimic this process, there has been an effort to grow endothelial cells on the surface of synthetic grafts. However, endothelial cells are expensive and difficult to grow on synthetic surfaces. Furthermore, there is no guarantee that the presence of endothelial cells will necessarily improve the patency of small caliber vascular conduits. Because collagen and fibronectin are known to promote the growth of many human cells including endothelial cells, the first attempt has been to coat the interior surface of these synthetic grafts with collagen, fibronectin, or a mixture of these two components.

For example, Sorin Biomedical of Italy markets a Dacron vascular graft that has been impregnated with bovine collagen. While this technique works for larger diameter grafts with internal diameters of ≧6 mm, this coating is unsuccessful with smaller diameter conduits. While collagen coating can and often does promote the growth of endothelial cells on the surface, it does nothing to prevent or retard intimal hyperplasia. Guidoin et al, reporting in *ASAIO Journal Nov–Dec*; 42, 1996, compared collagen impregnated grafts with pre-clotted grafts used as controls when implanted in canine models for periods ranging from one month to six months. While the collagen impregnated grafts showed a presence of endothelial cells on the inner lumen after a 30 day implantation, they found that the collagen impregnated grafts had a significantly higher wall thickness for most of the implantation period when compared with the pre-clotted grafts. The authors concluded that collagen impregnated polyester prosthesis cannot be recommended as small diameter blood conduits.

Clapper et al, reporting in *Symposium, Society for Biomaterials*, 1994, used a mixture of fibronectin and collagen to coat 4 mm ePTFE grafts with wall porosity of 20 μm. Data from 30-day implantation in canine models were reported. The authors show that 88% of the surface was covered with endothelial cells and the patency was 88%. Guidoin and his coworkers, however, have shown that the healing response with collagen coatings changes significantly after 30 days, resulting in substantial thickening of the vessel wall despite the presence of a layer of endothelial cells on the luminal surface. Therefore, the presence of endothelial cell coverage cannot be taken as evidence that this method will yield grafts with improved long-term patency.

Another method for improving the patency of small diameter vascular grafts has been the use of Dacron scaffolds implanted in the cutaneous trunci muscle of sheep to grow ovine collagenous tissue around the graft. Such a technique was described by Werkmeister et al in *Transactions, Society for Biomaterials, April* 1994. The use of scaffolds to grow animal tissue for human implantation is prone to poor quality control and is often expensive. Yet another method for fabricating small diameter vascular grafts involves combining two different layers of collagenous material as described by Termin et al, *Transactions, Society for Biomaterials, April* 1994. It is well known that composites manufactured from biological sources and used as blood conduits are prone to degradation and failure from aneurysms. Therefore this method does not offer a viable solution either. It is well known to those skilled in the art, that materials derived from animal tissue are also prone to calcification, thus significantly reducing the effectiveness of devices fabricated from such sources.

In U.S. Pat. No. 4,842,575, herein incorporated by reference, synthetic vascular grafts are impregnated with collagen. As described in earlier references, the use of collagen impregnation does not lead to improved patency of small caliber vascular conduits. In U.S. Pat. Nos. 5,643,712 and 5,880,090, herein incorporated by reference, the grafts are seeded with endothelial cells. While such coating may offer improved resistance to thrombosis, such coatings have not reduced intimal hyperplasia and thus do not guarantee improved patency of these small caliber vascular conduits. In U.S. Pat. No. 5,851,229, herein incorporated by reference, the inventors describe a bio-resorbable sealant for porous vascular grafts. The material used is a water absorbing polymer called a hydrogel. While such a coating can provide sealing action, it does not necessarily provide the needed anti-thrombogenic behavior, nor do such coatings reduce smooth muscle cell proliferation and intimal hyperplasia.

Greisler et al, *Biomaterials* 1996, Vol. 17, No. 3, studied the effects of impregnating ePTFE grafts, which have porous walls, with a mixture of Fibrin Glue, Acidic Fibroblast Growth Factor, and heparin on endothelial growth and intimal hyperplasia. This mixture appears to allow proliferation of endothelial cells on the luminal surface and in the presence of high concentration of heparin, reduce smooth muscle cell proliferation by 12%. While this reduction in smooth muscle cell proliferation is significant, it is not entirely sufficient for long-term patency. Greisler et al, in *Surfaces in Biomaterials Symposium* 1994, also examined the wash out kinetics of this mixture using $^{125}$I labeled Acidic Fibroblast Growth Factor and found that 86% of the mixture was washed out from the graft within fourteen days. By the end of 30 days, 96% of the mixture had been washed out from the graft. Thus, the effect of this approach appears to decrease exponentially with elapsed time.

Therefore, what is needed is a small diameter vascular conduit with diameters $\leq 5$ mm and which has (i) a luminal surface that is permanently non-thrombogenic, (ii) a graft structure such that smooth muscle proliferation and consequent intimal hyperplasia is substantially reduced or eliminated, and (iii) a graft structure that allows integration of the graft into the surrounding tissue.

SUMMARY OF THE INVENTION

The present invention substantially reduces or overcomes all of the problems associated with the prior art. The invention provides a novel multi-zone, multifunctional graft with two or more zones that have different chemical and biological characteristics. The present invention further provides a graft with these characteristics where the biological and chemical properties of the different zones are substantially independent of one another. The present invention further provides a vascular conduit that has of an inner zone that is permanently non-thrombogenic and anti-proliferative, and one or more outer zones that allow for beneficial tissue in-growth and sealing of the graft to prevent leakage. The small diameter vascular conduits of the present invention containing these different zones may be fabricated from woven or knitted Dacron, extruded porous PTFE, from polyurethane polymer, or other similar materials, and the structure of these conduits so modified as to provide these different zones. One embodiment contains an inner non-thrombogenic layer and an outer thrombogenic layer, optionally containing a growth agent. A second embodiment contains a third intermediate layer having a growth agent impregnated therein.

DETAILED DESCRIPTION OF THE INVENTION

The vascular graft of the present invention offers unique performance characteristics not found with products prepared by prior art methods. This is accomplished by creating two or more zones with different and substantially independent chemical and biological characteristics within the body of the graft. The vascular conduits of the present invention containing these different zones may be fabricated from any suitable material, including biocompatible plastics such as woven or knitted Dacron, extruded porous PTFE, from polyurethane polymer, or other similar materials. The material is preferably formed into a tubular structure and then treated and/or modified so as to provide these different zones.

Figure 1:
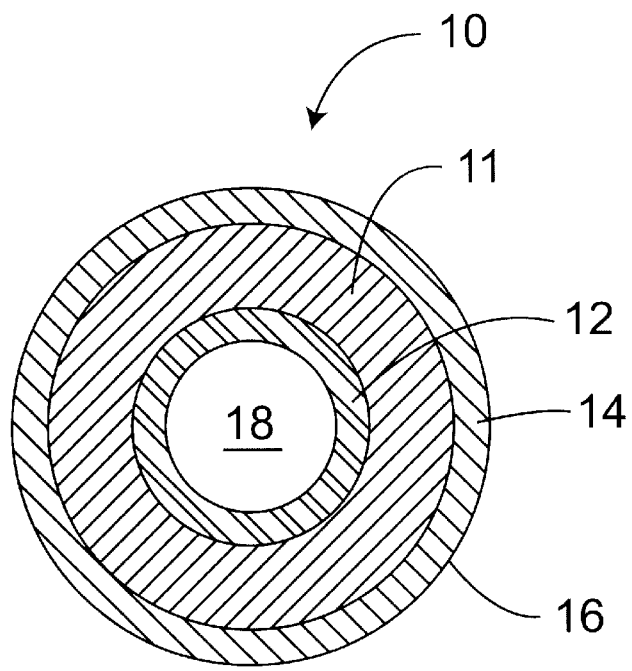
FIG. 1 is a cross section of a graft having two active zones.
Figure 2:
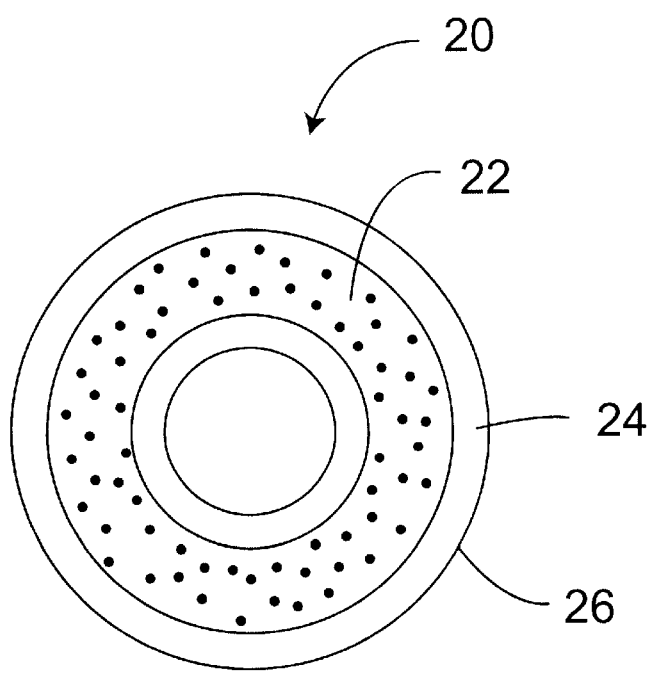
FIG. 2 is a cross section of a graft having three active zones.

The innermost layer or zone 12 that is in intimate contact with the blood flowing through the lumen 18 of the graft 10, also called the luminal layer, has chemical and biological properties that render the surface permanently non-thrombogenic. This layer or zone 12 is shown in FIG. 1 and FIG. 2. This is accomplished by chemically binding very high concentrations of agents that are non-thrombogenic to the base material 11 used in fabricating the graft 10. In addition, other agents are bound to the substrate material 11 in this zone 12 that prevent proliferation of undesirable cells, such as smooth muscle cells. It will be appreciated by those skilled in the art that there are likely to be therapeutic agents that provide both functions within a single biological compound that is bound to the surface. Thus, the zone 12 may contain one or more therapeutic agents chemically and permanently bound to the surface such that they prevent thrombosis and retard the proliferation of platelets and smooth muscle cells. Since the non-thrombogenic behavior of the graft surface depends on the concentration or dose of the therapeutic agent present, one key aspect of the present invention is that this agent is present in high concentrations. Since heparin obtained from animal sources is commonly used as a therapeutic agent for preventing thrombosis, one measure of a high concentration is that amount bound to surface that is in excess of 0.5 IU/cm$^2$ (International Units/square centimeter) as measured by an ATIII response test and preferably in excess of 3.0 IU/cm² as measured by an ATIII response test. It will be appreciated by those skilled in the art that other non-thrombogenic agents or other therapeutic agents may also be used. For example, hirudin or variations of the hirudin molecule may also be used in place of heparin as a non-thrombogenic agent. It should be noted that other agents may require different thresholds to be considered to be present in high concentrations. The thickness of the first layer or zone 12 can be ≦100 μm and preferably ≦25 μm. The first zone 12 plays a key role in preventing thrombosis and proliferation of smooth muscle cells. In this way the long-term patency of the graft 10 will be assured.

The second zone 14 consists of agents that may be chemically bound to the base material 11 of the graft, but this requirement is not mandatory. The second layer or zone 14 has as its main function, allowing infiltration of cells from the exterior environment into the wall of the graft 10 to create beneficial tissue. This can manifest itself as the growth of host collagen within the walls of the graft 10 and the potential migration of capillaries into the interstitial spaces of the graft wall 16. This is achieved by incorporating cell growth agents such as fibronectin, laminin or bovine collagen or analogs and variations of these materials in the wall of the synthetic graft 10. Some of the growth agents may also have thrombogenic properties.

The second zone 14 may also contain agents, such as thrombin, that promote thrombosis when the grafts 10 prepared according to this invention have of only two active zones 12, 14 as shown in FIG. 1 to insure that there is no leakage of blood from the graft 10 when porous materials are employed in fabricating the graft 10. In this case, the thickness of the second zone 14 also constitutes the bulk of the graft wall 16 and may be anywhere from 100 μm to 500 μm, and more preferably between 200 μm and 400 μm.

When preparing grafts 20 with three layers according to this invention, as shown in FIG. 2, an intermediate layer 22, devoid of any agents that promote thrombosis, is present. In this embodiment, the intermediate layer 22 only contains cell growth agents such as Fibronectin, Laminin, or collagen or analogs and variations of these materials in the wall 26 of the graft 10. In the three zone structure illustrated in FIG. 2, the outermost zone 24 contains a mixture of animal collagen such as bovine collagen and thrombin to promote clotting and thus seal the graft 10 and prevent blood leakage until the graft 10 is integrated into the surrounding tissue. The thickness of this outer zone 24 can be ≦100 μm and is preferably ≦25 μm.

It will be readily apparent to those skilled in the art that there may be several approaches to fabricating such a multizone, multifinctional small diameter vascular conduit as described in this invention. The following examples serve to illustrate a few of these approaches.

Example 1

In one embodiment of this invention, a woven Dacron tubing of internal diameter of 3 mm and a wall thickness of 350 μm is first treated in a RF plasma reactor so as to modify the internal surface of the tubing and create a high concentration of amine groups on the surface. It will be apparent to those skilled in the art that there are several methods for creating such a high concentration of reactive amine groups. One such method uses a plasma deposited film network as described in U.S. Pat. No. 5,723,291 herein incorporated by reference. To these amine groups an anti-coagulant such as heparin containing functional groups reactive to the amines is covalently and chemically bound to the surface. Depending on the base material 11 and process used to form the layer, the material may be a coating which is chemically bonded to the base material 11 or the layer may be at least partially incorporated into the base material 11, thereby creating the first zone within the base material 11.

After attachment of the heparin to the interior surface, a water soluble polymer such as polyethylene glycol with a cell growth agent such as fibronectin is infused into the first layer of the graft structure. The fibronectin serves to allow growth of beneficial cells such as endothelial cells to grow in the area next to the anti-coagulant inner surface.

The exterior surface of the graft is coated with collagen or a mixture of collagen and thrombin to ensure that any blood seeping through the pores of the graft contact the collagen or collagen-thrombin mixture and promote clotting to seal the graft. The exterior of the graft may also be sealed with a thin coating of polymers formed in situ using peroxide initiated crosslinking of vinyl acrylates.

While the above description provides a means for fabricating a multizone, multifunctional vascular graft, it is to be understood that this description is illustrative only and not limiting of the disclosed invention. It will be appreciated that various methods to produce such a multifunctional, multizone synthetic vascular conduit will fall within the scope and spirit of this invention.

What is claimed is:

1. A vascular graft having a lumen passing therethrough, said graft comprising:
   a tubular wall structure including:
      a first non-thrombogenic layer formed of a first material and forming the lumen, an interior surface of said first layer being treated with a non-thrombogenic agent, said first layer having a thickness less than 100 μm, and
      a second thrombogenic layer outside said first layer and formed of a second material, an exterior surface of said second layer being treated with a thrombogenic agent, said second layer having a thickness less than 100 μm.

2. The vascular graft of claim 1 wherein said first non-thrombogenic layer is formed by chemically binding said non-thrombogenic agent to said first material, thereby permanently forming said first non-thrombogenic first layer.

3. The vascular graft of claim 2 wherein said first material and second materials are both a biocompatible plastic.

4. The vascular graft of claim 3 wherein said biocompatible plastic is chosen from a group of materials consisting of Dacron, polytetrafluoroethylene (PTFE), and polyurethane polymer.

5. The vascular graft of claim 2 wherein a therapeutic agent is bound to said first material.

6. The vascular graft of claim 5 wherein said therapeutic agent is chosen to inhibit proliferation of undesirable cells.

7. The vascular graft of claim 5 wherein said therapeutic agent is chosen to inhibit proliferation of platelets.

8. The vascular graft of claim 5 wherein said therapeutic agent is chosen to inhibit proliferation of smooth muscle cells.

9. The vascular graft of claim 2 wherein said non-thrombogenic agent is heparin.

10. A vascular graft having a lumen passing therethrough, said graft comprising:
    a tubular wall structure including:
       a first non-thrombogenic layer formed of a first material and forming the lumen, an interior surface of said first layer being formed by chemically binding a non-thrombogenic agent to said first material, thereby permanently forming said first non-thrombogenic first layer, said non-thrombogenic agent having a concentration of at least 0.5 IU/cm$^2$ as measured by an ATIII response test, a second thrombogenic layer outside said first layer and formed of a second material, an exterior surface of said second layer being treated with a thrombogenic agent.

11. The vascular graft of claim 10 wherein said non-thrombogenic agent is heparin and has a concentration of at least 3.0 IU/cm$^2$ as measured by an ATIII response test.

12. The vascular graft of claim 10 wherein said first layer has a thickness less than 100 μm and said second layer has a thickness less than 100 μm.

13. The vascular graft of claim 1 wherein said first layer has a thickness less than 25 μm and said second layer has a thickness less than 25 μm.

14. The vascular graft of claim 1 wherein said thrombogenic agent is chemically bound to said second material of said second layer.

15. The vascular graft of claim 1 further comprising a therapeutic agent bound to said second layer.

16. The vascular graft of claim 15 wherein said therapeutic agent is chosen to promote infiltration of cells from existing tissue into said second layer of said graft, thereby creating beneficial tissue attachment.

17. The vascular graft of claim 15 wherein said therapeutic agent is chosen to promote host collagen.

18. The vascular graft of claim 15 wherein said therapeutic agent is chosen to promote growth of capillaries into the interstitial spaces of the graft wall.

19. The vascular graft of claim 1 wherein said second layer includes a growth agent.

20. The vascular graft of claim 19 wherein said growth agent is chosen from the group of growth agents consisting of fibronectin, laminin and collagen.

21. The vascular graft of claim 1 further comprising a third layer located between said first layer and said second layer, said third layer containing a growth agent.

22. The vascular graft of claim 21 wherein said growth agent is chosen from the group of growth agents consisting of fibronectin, laminin and collagen.

23. The vascular graft of claim 1 wherein said first material and said second material are the same.

24. A vascular graft having a lumen passing therethrough, said graft comprising:

a first non-thrombogenic layer forming the lumen, said first non-thrombogenic layer having a thickness less than 100 μm, a second growth layer outside said first layer, said second layer having a thickness in the range of 100 μm to 500 μm, and a third thrombogenic layer outside both said first and said second layer, said third layer having a thickness less than 100 μm.

25. The vascular graft of claim 24 wherein said first non-thrombogenic layer is formed by chemically binding a non-thrombogenic agent to a base material, thereby permanently forming said first non thrombogenic layer.

26. The vascular graft of claim 25 wherein an additional therapeutic agent is bound to said base material.

27. A vascular graft having a lumen passing therethrough, said graft comprising:

a first non-thrombogenic layer forming the lumen, said first non-thrombogenic layer formed by chemically binding a non-thrombogenic agent to a base material, thereby permanently forming said first non thrombogenic layer, and wherein said non-thrombogenic agent has a concentration of at least 0.5 IU/cm$^2$ as measured by an ATIII response test, a second growth layer outside said first layer, and a third thrombogenic layer outside both said first and said second layer.

28. The vascular graft of claim 27 wherein said non-thrombogenic agent has a concentration of at least 3.0 IU/cm$^2$ as measured by an ATIII response test.

29. The vascular graft of claim 27 wherein said first layer has a thickness less than 100 μm, said second layer has a thickness in the range of 100 μm to 500 μm, and said third layer has a thickness less than 100 μm.

30. The vascular graft of claim 24 wherein said first layer has a thickness less than 25 μm, said second layer has a thickness in the range of 200 μm to 400 μm, and said third layer has a thickness less than 25 μm.

31. The vascular graft of claim 24 wherein a thrombogenic agent is chemically bound to a base material of said second layer.

32. The vascular graft of claim 31 wherein said third layer also includes a growth agent.

33. The vascular graft of claim 24 wherein a growth agent is impregnated within said second layer.

34. A vascular graft, comprising:

a tubular body having a first end, a second end, a wall, an interior surface, an exterior surface and a lumen passing therethrough, said tubular body formed of a biocompatible plastic, said wall of said tubular body treated such that a first inner layer and a second outer layer are formed, said first layer formed of a non-thrombogenic agent chemically bound to said biocompatible plastic on said interior surface of said tubular body, thereby inhibiting the proliferation of undesirable cells within said vascular graft, said first layer having a thickness of less than 25 μm, said second layer formed of a thrombogenic material chemically bound to said biocompatible plastic on said exterior surface of said tubular, thereby promoting the infiltration of desirable cells into said second layer, said second layer having a thickness of less than 25 μm.

35. The vascular graft of claim 34 wherein a growth agent is located within said wall of said tubular body intermediate said first layer and said second layer, thereby creating a third active layer, said third layer having a thickness in the range of 200 μm to 400 μm.

36. The vascular graft of claim 34 wherein said vascular graft has an internal diameter 5.0 mm or smaller.

* * * * *